(12) United States Patent
Dale et al.

(10) Patent No.: US 10,889,846 B2
(45) Date of Patent: *Jan. 12, 2021

(54) METHODS AND DEVICES TO DETECT THE PRESENCE OF A CONDITION ASSOCIATED WITH ATP DEPLETION IN A SUBJECT

(71) Applicant: Sarissa Biomedical Limited, Coventry (GB)

(72) Inventors: Nicholas Dale, Coventry (GB); Chris Imray, Coventry (GB); Bruno Frenguelli, Coventry (GB)

(73) Assignee: SARISSA BIOMEDICAL LIMITED, Coventry (GB)

( * ) Notice: Subject to any disclaimer, the term of this patent is extended or adjusted under 35 U.S.C. 154(b) by 194 days.

This patent is subject to a terminal disclaimer.

(21) Appl. No.: 15/580,582

(22) PCT Filed: Jun. 3, 2016

(86) PCT No.: PCT/GB2016/051641
§ 371 (c)(1),
(2) Date: Dec. 7, 2017

(87) PCT Pub. No.: WO2016/198839
PCT Pub. Date: Dec. 15, 2016

(65) Prior Publication Data
US 2018/0155754 A1  Jun. 7, 2018

(30) Foreign Application Priority Data
Jun. 9, 2015  (GB) .................................. 1509974.0

(51) Int. Cl.
*G01N 27/327* (2006.01)
*C12Q 1/00* (2006.01)
(Continued)

(52) U.S. Cl.
CPC ............. *C12Q 1/005* (2013.01); *C12Q 1/004* (2013.01); *C12Q 1/26* (2013.01); *C12Q 1/34* (2013.01);
(Continued)

(58) Field of Classification Search
CPC .................... G01N 27/327–3272; C12Q 1/004
See application file for complete search history.

(56) References Cited

FOREIGN PATENT DOCUMENTS

| WO | 2008081193 | 10/2008 |
|----|------------|---------|
| WO | 2009020860 | 2/2009 |
| WO | 2014087137 | 6/2014 |

OTHER PUBLICATIONS

Issel et al., "Hypoxanthine levels in amniotic fluid: An indicator of fetal hypoxia?", J. Perinat. Med. 10 (1982) 221 (Year: 1982).*
(Continued)

*Primary Examiner* — Alexander S Noguerola
(74) *Attorney, Agent, or Firm* — Brannon Sowers & Cracraft PC

(57) ABSTRACT

The invention provides a method of determining a predisposition to a condition associated with ATP depletion, such as an ischaemic event, in a subject comprising: a. measuring the concentration of one or more purines in a body fluid of the subject, the purines being selected from adenosine, inosine, hypoxanthine, xanthine and ATP, and b. comparing the measured concentration with a threshold concentration of the one or more purines, wherein the threshold concentration is preferably in the range 2 [micro]M to 8 [micro]M and wherein a measured concentration higher than the threshold concentration indicates the presence of ischaemia.

22 Claims, 4 Drawing Sheets

(51) Int. Cl.
    *G01N 33/53*     (2006.01)
    *G01N 33/543*     (2006.01)
    *C12Q 1/26*     (2006.01)
    *C12Q 1/34*     (2006.01)
    *C12Q 1/48*     (2006.01)

(52) U.S. Cl.
    CPC ........ *C12Q 1/48* (2013.01); *C12Y 117/03002* (2013.01); *C12Y 204/02001* (2013.01); *C12Y 305/04004* (2013.01); *G01N 27/3271* (2013.01); *G01N 33/5308* (2013.01); *G01N 33/5438* (2013.01); *G01N 2800/7019* (2013.01)

(56) References Cited

OTHER PUBLICATIONS

Martin et al., "High adenosine plasma concentration as a prognosis index for outcome in patients with septic shock," Crit Care Med 2000 vol. 28, No. 9, pp. 3198-3202 (Year: 2000).*

Rai et al., "High concentration of adenosine in human visceral leishmaniasis despite increased ADA and decreased CD73," Parasite Immunology, 2011, 33, 632-636 (Year: 2011).*

PCT Search Report prepared for PCT/GB/2016/051641, dated Sep. 9, 2016.

Farthing, Don E., Christine A. Farthing, and Lei Xi. "Inosine and hypoxanthine as novel biomarkers for cardiac schemia: From bench to point-of-care." Experimental Biology and Medicine 240.6 (2015): 821-831.

Mei, David A., Garrett J. Gross, and Kasem Nithipatikom. "Simultaneous determination of adenosine, inosine, iypoxanthine, xanthine, and uric acid in microdialysis samples using microbore column high-performance liquid chromatography with a diode array detector." Analytical biochemistry 238.1 (1996): 34-39.

Berne, Robert M., Rafael Rubio, and Richard R. Curnish. "Release of adenosine from ischemic brain." Circulation Research 35.2 (1974): 262-271.

Van Wylen, D. G. "Effect of ischemic preconditioning on interstitial purine metabolite and lactate accumulation during myocardial ischemia." Circulation 89.5 (1994): 2283-2289.

Swanström, Sten, and Lars-Eric Bratteby. "Hypoxanthine as a test of perinatal hypoxia as compared to lactate, base deficit, and pH." Pediatric research 16.2 (1982): 156-160.

Matheme, G. Paul, et al. "Interstitial transudate purines in normoxic and hypoxic immature and mature rabbit hearts." Pediatric research 28.4 (1990): 348-353.

Bøhmer, T., J. Kjekshus, and P. Vaagenes. "Biochemical indices of cerebral ischemic injury." Scandinavian journal of clinical and laboratory investigation 43.3 (1983): 261-265.

PCT Search Report prepared for PCT/GB2016/051638, dated Sep. 13, 2016.

Dale, Nicholas, and Bruno G. Frenguelli. "Measurement of purine release with microelectrode biosensors." Purinergic signalling 8.1 (2012): 27-40.

Tian, Faming, Enrique Llaudet, and Nicholas Dale. "Ruthenium purple-mediated microelectrode biosensors based on sol-gel film." Analytical chemistry 79.17 (2007): 6760-6766.

Weigand, Markus A., et al. "Adenosine a Sensitive Indicator of Cerebral Ischemia during Carotid Endarterectomy." Anesthesiology: The Journal of the American Society of Anesthesiologists 91.2 (1999): 414-421.

Pasini, Franco Laghi, et al. "Increase in plasma adenosine during brain ischemia in man: a study during transient schemic attacks, and stroke." Brain research bulletin 51.4 (2000): 327-330.

Hong, Zhang. "1,\Murong Shengxing 1,\Liu Youyao 2, et al (1. Department of Neurology, 1st Affiliated Hospital,\2. Department of Biochemistry, Fujian Medical University, Fuzhou, 350005); Changes of NO and cGMP in Different Brain Regions at Early Stage during Cerebral Ischemia in Rats [J]." Journal of Fujian Medical University 3 (1998).

Galvani, Marcello, Donatella Ferrini, and Filippo Ottani. "Natriuretic peptides for risk stratification of patients with acute coronary syndromes." European journal of heart failure 6.3 (2004): 327-333.

"Expression difference between high-sensitivity C-reactive protein (hs-CRP) and N-terminal pro-brain natriuretic peptide (NT-proBNP) precursors in acute coronary syndromes (ACS) of different degrees" China Academic Journal Electronic Publishing House, May 14, 2013; 2540-2541; (English Translation of Abstract).

* cited by examiner

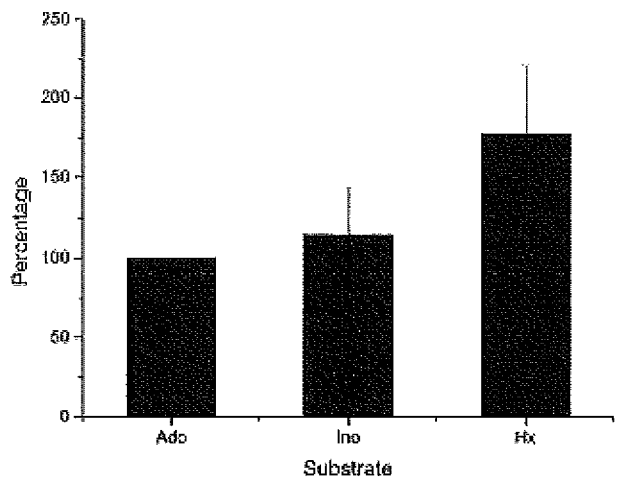
Figure 4a
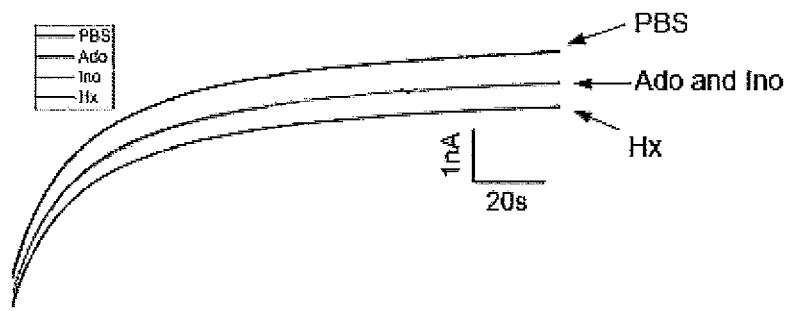
Figure 4b
| eqvt [Ado] | [Ado] | [Ino] | [Hx] |
|---:|---:|---:|---:|
| 2.15 | 1 | 1 | |
| 2.95 | | 1 | 1 |
| 2.8 | 1 | | 1 |
| 3.95 | 1 | 1 | 1 |
| 2 | 2 | | |
| 2.3 | | 2 | |
| 3.6 | | | 2 |
| 4.3 | 2 | 2 | |
| 5.6 | 2 | | 2 |
| 5.9 | | 2 | 2 |
| 7.9 | 2 | 2 | 2 |
Figure 4c

METHODS AND DEVICES TO DETECT THE PRESENCE OF A CONDITION ASSOCIATED WITH ATP DEPLETION IN A SUBJECT

CROSS-REFERENCE TO RELATED APPLICATION

This application is a U.S. national entry application under 37 C.F.R. § 371(b) of International Application Serial No. PCT/GB2016/051641 filed on Jun. 3, 2016, which claims the right of priority and benefit under 35 U.S.C. §§ 119 & 365 of GB Patent Application No. 1509974.0 filed on Jun. 9, 2015, the disclosures of which are incorporated herein by reference in their entirety. This application also cross-references co-pending International Application Serial No. PCT/GB2016/051638 filed on Jun. 3, 2016, which claims the right of priority and benefit under 35 U.S.C. §§ 119 & 365 of GB Patent Application No. 1509973.2 filed on Jun. 9, 2015, the disclosures of which are incorporated herein by reference in their entirety.

FIELD

The present invention relates to apparatus and methods to measure a physiological condition of a subject, and in particular to measure the presence of a condition associated with ATP depletion, such as ischaemia in a subject such as a human patient.

BACKGROUND

Ischaemia is a restriction in blood supply to tissues which results in a shortage of oxygen and glucose needed for cellular metabolism. Typically ischemia results from occlusion or rupture of blood vessels, with resultant damage to or dysfunction of tissue. A range of disease conditions result from, or result in, ischaemia, including acute conditions such as ischaemic stroke, transient ischaemic attack (TIA), and cardiovascular disease such as myocardial infarction (MI). Ischaemia may also result from chronic conditions including vascular insufficiency such as critical limb ischaemia (CLI) in diabetes, chronic cerebral ischaemia resulting from vascular disease and chronic ischaemic heart disease (IHD). In cardiac disease this is characterised for example by angina and ischaemic cardiomyopathy. Ischaemia may be present in a locus of a subject's body, and may be difficult or impossible to detect using prior art techniques. Such chronic ischaemic disease may be characterized by stable symptoms over a period of months, years, or even decades, and in its early stages may be asymptomatic or symptoms may be mild and unnoticed. However, it predisposes towards later acute ischaemic disease, and so early detection would have significant clinical value.

Cellular metabolism is driven by the disequilibrium between ATP and ADP (Nicholls D G, Ferguson S J. Bioenergetics 2. London: Academic Press; 1992) (all references cited herein are incorporated by reference), and so enzymatic pathways exist in cells to rapidly remove ADP and in effect convert it to adenosine (Sims R E, Dale N. Activity-Dependent Adenosine Release May Be Linked to Activation of Na(+)-K(+) ATPase: An In Vitro Rat Study. PLoS One 2014; 9(1)) and the downstream purines inosine and hypoxanthine. In ischaemic disease, tissue hypoxia results in the loss of the ability of cells to make ATP and results in the intracellular accumulation of adenosine and downstream purines, which can then efflux via equilibrative transporters. Although a few studies have examined whether purine levels in blood increase during acute events such as stroke (Laghi Pasini F et al. Increase in plasma adenosine during brain ischemia in man: a study during transient ischemic attacks, and stroke. *Brain Res Bull* 2000; 51(4): 327-30) and brain ischaemia during carotid endarchectomy procedures (Weigand M A, et al. Adenosine: a sensitive indicator of cerebral ischemia during carotid endarterectomy. *Anesthesiology* 1999; 91(2): 414-21), this has not been widely studied.

While it is known from the prior art that levels of purines are elevated in conditions of acute local hypoxia/ischaemia, there has been no link in the prior art between chronic ischaemia and raised purine levels in apparently healthy subjects. These previous studies have relied on measurements made in clinical analysers remote from the subject and, owing to the rapid breakdown of purines by enzymes in whole blood, samples need to be frozen immediately after being taken, transported frozen to the instrument, thawed and then separated into plasma; thawing and separation are slow processes, which leads to significant breakdown of purines in the sample. This sequence of events leads to insensitive and unreliable measurements and is not suited to routine clinical practice. It is an object of the present invention to provide methods and devices to allow measurement of purines to be related to the presence of ischaemia in a subject such as a human patient, and in some embodiments to the presence of a disease condition in the subject or the risk of the subject developing such a condition.

DESCRIPTION OF THE INVENTION

According to a first aspect, the invention provides a method of determining a predisposition to a condition associated with ATP depletion, typically an ischaemic event, in a subject comprising:

measuring the concentration of one or more purines in a body fluid of the subject, the purines being selected from adenosine, inosine, hypoxanthine, xanthine and ATP, and comparing the measured concentration with a threshold concentration of the one or more purines, wherein the threshold concentration is typically in the range around 2 µM to around 8 µM and wherein a measured concentration higher than the threshold concentration indicates the presence of the condition, for example ischaemia.

The condition may be a condition associated with ATP breakdown products being present in bodily fluids such as blood. These include anoxia and hypoxia, glucose deprivation (such as hypoglycemia and aglycemia, inflammation, infection, swelling (such as fluid accumulation/hydrocephaly), neurodegenerative conditions (such as Alzheimer's and Parkinson's diseases) and multiple sclerosis. The condition may be an ischaemic event such as a cerebral ischaemic event.

The method typically identifies an increased risk that the subject will develop a condition associated with ATP depletion, such as an ischaemic event. The subject typically does not have obvious physical symptoms of a condition associated with ATP depletion, such as ischaemia. For example, the subject does present physical symptoms of ischaemia, does not present with physical symptoms of a stroke, transient ischaemic attack (TIA), gangrenous limb, heart attack or signs of a traumatic head injury. Apparent physical symptoms include sudden weakness in a limb; confusion or having trouble speaking; sudden trouble seeing in one or both eyes; sudden trouble walking dizziness; and sudden severe headaches. The stroke may be an ischaemic stroke, a haemorrhagic stoke.

The subject may have a condition which itself has an increased risk of ischaemia, such as diabetes, high blood pressure, atrial fibrillation or stenosis of the artery, or over 50 years of age.

The method allows the identification of an otherwise non-apparent ischaemic event or shows an increase in risk that an event will occur.

A determination that ischaemia is present in a subject may indicate a probability that the subject has a chronic ischaemic medical condition or may indicate a degree of risk that the subject may later develop an acute ischaemic medical condition.

In some embodiments the measured concentration may be used to indicate the said probability or degree of risk, a lower measured concentration indicating a lower probability or degree of risk and a higher concentration indicating a higher probability or degree of risk.

In some embodiments the threshold concentration is in the range 2 µM to 6 µM, in some embodiments in the range 4 µM to 8 µM, in some embodiments in the range 2 µM to 4 µM, and in some embodiments in the range 3 µM to 4 µM.

In some embodiments the method comprises comparing a measured concentration with the threshold concentration and using the difference between the measured concentration and the threshold concentration to determine a probability that a covert ischaemic condition is present in the subject or a risk that the subject may later develop an acute ischaemic medical condition. For example, a measured concentration far above the threshold may indicate a higher said probability or risk and a measured concentration close to the threshold may indicate a lower probability or risk.

According to the embodiment, a chronic medical condition may be chronic cerebral ischaemia resulting from vascular disease, cardiovascular disease such as chronic ischaemic heart disease (IHD) characterised for example by angina and ischaemic cardiomyopathy, critical limb ischaemia (CLI), hypoxic tumours in cancer and bedsores in immobile patients, and an acute ischaemic medical condition may be ischaemic stroke, transient ischaemic attack (TIA), myocardial infarction (MI) and deep-vein thrombosis.

A subject may be a post-partum human subject, such as child of age over 3 months, 6 months, 1 year, 5 years or 10 years, or an adult of age 15 years or more.

A subject may be a neonate, or a baby in utero. The method may comprise measuring the purine concentration in a body fluid of a baby at one or more occasions before, during or after birth in order to determine a hypoxic condition of the baby.

Typically a subject may present without classical symptoms of acute ischaemic disease, such as symptoms of stroke like slurred speech, unilateral weakness or paralysis, one sided facial paralysis or unconsciousness, or of MI, and the method may be used to determine the presence of ischaemia, such as an occult or chronic ischaemic medical condition.

In this way the method provides a means to determine that covert ischaemia is present in the subject, in which the presence of ischaemia or a medical condition causing or resulting from it is not apparent from a physical examination of the subject.

In some embodiments the invention provides a method of diagnosing ischaemia or an occult ischaemic medical condition, and in some embodiments provides a method of prognosis in which a measured concentration of one or more purines indicates a prognostic finding, for example that a higher measured concentration indicates a higher risk of progression of the disease.

In this way the method provides a means to determine that covert ischaemia is present in the subject, in which presence of ischaemia or a medical condition causing or resulting from it is not apparent from a physical examination of the subject.

The method also provides a means of prioritising a subject for treatment or for further investigation, a purine concentration greater than the threshold indicating a higher priority, and a concentration below the threshold indicates a lower priority or no need for further action. The method further provides a means of allocating a subject to a subpopulation of subjects, a purine concentration greater than the threshold being used to allocate the subject to a first subpopulation, such as a higher risk subpopulation, and a concentration below the threshold being used to allocate the subject to a second subpopulation, such as a lower risk subpopulation.

The threshold concentration may be selected to provide suitable discrimination between higher and lower risk for a patient population as a whole or for a subpopulation. In some embodiments the method comprises allocating a subject to a subpopulation and then selecting a further threshold concentration for use in the method that is suitable for the said subpopulation. For example, the subpopulation may comprise subjects having a specific medical condition or suspected medical condition, and may be characterised by other subject-specific factors such as age, weight, sex or smoking/non-smoking.

A threshold concentration may be selected for use in the method according to the embodiment. A threshold concentration may be selected in the range 2 to 8 uM, 4 to 8 uM or 3 to 4 uM, such as 2.0, 2.2, 2.4, 2.5, 2.6, 2.8, 3.0, 3.2, 3.4, 3.5, 3.6, 3.8, 4.0, 4.5, 5.0, 5.5, 6.0, 6.5, 7.0, 7.5, or 8.0 uM. The threshold concentration may be selected according to a subpopulation of subjects with whom the method is to be used. The threshold concentration may be selected to give an appropriate selectivity and specificity to the method, in determining the presence of ischaemia in a subject. The threshold may be selected to give a desired balance, such as a ratio, between false positive and false negative results. In some embodiments the method comprises modifying the threshold concentration in the light of observation of outcomes resulting from such determination.

Herein for clarity and brevity a concentration being greater than a threshold concentration is taken to include that the concentration is equal to the threshold concentration. In some embodiments a concentration being lower than a threshold concentration includes that the concentration is equal to the threshold concentration.

According to the embodiment, a body fluid may be whole blood, serum, plasma or cerebrospinal fluid. Typically a body fluid is whole blood, serum or plasma. Blood, serum or plasma may be arterial blood, venous blood and may be peripheral blood. The body fluid may be diluted or mixed with a further liquid or compound before a measurement is made.

In various embodiments, the measured concentration and the threshold concentration may be
  (i) those of a single purine selected from the said purines, measured individually;
  (ii) a total of the concentrations of two or more said purines, each measured individually;
  (iii) a weighted sum of the concentration of two or more said purines, each measured individually, for example of the form:

total concentration=$A\times$[purine(1)]+$B\times$[purine(2)],
where square brackets denote concentration;

(iv) an equivalent total purine concentration measured by a measurement method responsive to two or more said purines, the total purine measurement being calibrated relative to the response of the method to a single purine;

(v) a weighted sum of two or more said measurements of total purines, for example of the form total concentration=$A\times$[purine(1) and purine(2)]+$B\times$[purine(3) and purine(4)].

In methods (iv) and (v) the response of the measurement method may be such that the response to a second purine is a known function, such as a ratio, of the response to the first, such that when calibrated with a known concentration of the first purine, the response to the second purine is known.

In some embodiments the measured and threshold concentrations are total purine concentrations derived from a measurement method sensitive to three, four or five of the said purines, wherein the measurement is calibrated relative to the response to a calibration purine, the measurement method having a known ratio of the response to the calibration purine to the response to each of the remaining purines.

For example the said three purines may be adenosine, inosine and hypoxanthine and the calibration purine may be one of the three purines, typically adenosine. The said four purines may be adenosine, inosine, hypoxanthine and xanthine and the calibration purine may be one of the four purines, typically adenosine.

In such methods the ratio of responses of the measurement method, or a measurement device such as a sensor, to hypoxanthine, xanthine and inosine to that of adenosine may be known from the parameters of the method or device, and the method may comprise comparing the response to all the purines present in the sample with the response to a known concentration of adenosine to derive a value of total purine concentration in terms of an equivalent concentration of adenosine.

For example, a measurement device such as a sensor may have a response S given by:

$S=A$[adenosine]+$B$[inosine]+$C$[hypoxanthine]+$D$[xanthine]

where the values of the calibration factors A, B, C and D are substantially constant with concentration, such that the ratios of the responses to each of inosine, hypoxanthine and xanthine to that of adenosine are constant values $b=B/A$, $c=C/A$ and $d=D/A$.

The measurement response $S_m$ to a combination of purines in a sample is:

$S_m=A$([adenosine]$m+b.$[inosine]$m+c.$[hypoxanthine]$m+d.$[xanthine]$m$)

The calibration response to a known concentration of adenosine [adenosine]$_{cal}$ is:

$S_c=A$[adenosine]$_{cal}$ $S_m$ may be expressed in terms of an equivalent concentration of adenosine, [adenosine]':

$S_m=S_c$([adenosine]'/[adenosine]$_{cal}$), where [adenosine]'=[adenosine]$m+b.$[inosine]$m+c.$[hypoxanthine]$m+d.$[xanthine]$m$ Accordingly, in some embodiments the measured concentration of total purines may be the equivalent concentration of adenosine, [adenosine]'.

For a measurement method which is equally sensitive to each purine, the factors b, c and d are all equal to 1 and [adenosine]' is simply the sum of the individual purine concentrations. Certain enzyme sensors comprising a cascade of enzymes to react each of the purines to a common measurand such as hydrogen peroxide may fall into this category, as will be discussed below. In general, a sensor may have different sensitivities to each purine, the factors b, c, and d being known from the inherent properties of the sensor or found by calibration during manufacturing.

Accordingly, in some embodiments the measured concentration of the said one or more purines is expressed in terms of an equivalent concentration of one purine, the response of the sensor being calibrated using the said purine, and the threshold concentration is a value of the said equivalent concentration.

Accordingly, in some embodiments the method comprises:

(i) measuring the measurement response of a measurement device responsive to more than one purine selected from adenosine, inosine, hypoxanthine, xanthine and ATP when contacted with a sample comprising a body fluid, (ii) measuring the calibration response of the measurement device to a calibration concentration of one of the said purines, (iii) deriving the equivalent concentration of the said one purine that would result in the same measurement response when present alone of the said purines in the sample, and (iv) comparing the said equivalent concentration with a threshold value of the equivalent concentration, wherein the threshold concentration is typically in the range 2 µM to 8 µM and wherein a measured equivalent concentration higher than the threshold concentration indicates the presence of the condition.

The measurement device may be a biosensor as described herein.

The measured concentration may be derived in terms of a value of concentration, or may be derived as a measured signal from the measurement device, the measured signal being calibrated in comparison with a calibration signal measured when a known concentration of a purine is present, the threshold concentration being expressed as a threshold value of the signal.

In some embodiments the method comprises:

(i) measuring a measurement signal from a measurement device when contacted with a plurality of purines in a sample of a body fluid from a subject, (ii) measuring a calibration signal when contacted with a calibration purine, (iii) using the measurement signal and the calibration signal to derive an equivalent signal representative of the equivalent concentration of the calibration purine, and (iv) comparing the equivalent signal with a threshold signal value representing a threshold equivalent concentration, wherein an equivalent signal greater than the threshold signal value indicates the presence of the condition in the subject.

In some embodiments the method comprises measuring the concentration of one or more purines independently of other purines, and comparing the measured concentration with a threshold concentration for the said purine. The purine may be one of adenosine, xanthine, inosine or ATP and the threshold concentration may be in the range 2 µM to 4 µM. The purine may be hypoxanthine and the threshold concentration may be in the range 2 µM to 8 µM.

The purines may be adenosine, inosine, hypoxanthine and xanthine, the calibration purine may be adenosine, and the threshold concentration may be in the range 2 µM to 8 µM.

The purines may be inosine, hypoxanthine and xanthine, the calibration purine may be inosine, and the threshold concentration may be in the range 2 µM to 8 µM.

The purines may be hypoxanthine and xanthine, the calibration purine may be hypoxanthine, and the threshold concentration may be in the range 2 µM to 8 µM.

In this way in some embodiments the actual concentration of each individual purine is not derived, and the measured concentration of the one or more purines is not necessarily a summation of the individual concentrations of the purines present in the sample; rather the measured concentration may be a value indicative of the total purine content of the sample, which is then compared with a threshold value to determine the presence of the condition such as ischaemia in the patient.

A change in the concentration of a purine in a body fluid of a subject may indicate covert ischaemia and may indicate progression or resolution of an ischaemic disease.

In some embodiments the method comprises:
measuring the concentration of one or more of the said purines at each of a first and a second time points,
comparing the change in measured concentration with a threshold value for the change and
determining that the condition is present in the subject if the rate of change is above the threshold value.

The threshold value of the change may be in the ranges 1 µM to 8 µM between the first and the second measurement, or 2 µM to 4 µM, or 1 µM to 3 µM between the first and the second measurement. The first and second measurement may be separated by a time interval in the range 1 day to 2 years, such as 1 to 12 weeks, 3 months to 6 months, 6 months to 2 years.

The change may be expressed as a rate of change over time. The threshold value of the rate of change may be in the range 1 µM to 8 µM per year, or 2 µM to 4 µM, or 1 µM to 3 µM, or above 8 µM per year.

An increase in purine concentration may indicate presence or progression of ischaemia and a decrease may indicate alleviation or resolution.

The change may be a change in the measured concentration of a single purine, or of the measured total concentration as described herein of two or more purines.

In some embodiments the method comprises
a. measuring the concentration of one or more said purines at each of a first and a second time points and
b. using a measured concentration at one time point together with the change in a measured concentration between the first and the second time points to determine the presence of acute ischaemic disorder in the subject.

The presence of ischaemia may be indicated by the combination of (i) a concentration of one or more purines being above a threshold concentration and (ii) a change in the measured concentration of one or more purines being above a threshold value for the change.

The method may comprise deriving a value indicative of the probability that ischaemia is present in a subject or the risk of the subject later developing an ischaemic medical condition. For example a value V may be derived from an equation of the form:

$V = A.[\text{purines}] + B.(\text{rate of change of }[\text{purines}])$, where A and B are constant or a function of further variables, such as a function of other risk factors for ischaemia specific for an individual or subpopulation of which the individual is a member.

In some embodiments the presence of ischaemia may be indicated by the combination of (i) a concentration of one or more purines above a threshold concentration and (ii) a rate of change of one or more purines above a threshold value of the rate of change. A value V as above may depend on the difference between the measured concentration or rate of change of concentration and the respective threshold values:

$$V = A.([\text{purines}] - \text{threshold concentration}) + B.(\text{rate of change of }[\text{purines}] - \text{rate of change threshold})$$

In this way the presence of ischaemia may be indicated with more confidence than for measurement of a concentration at a single time, which may arise from a confounding effect, by observing a trend leading towards a higher concentration. In some embodiments a lower threshold for the concentration measurement, which on its own might result in a false positive result, may be used together with a change between a first and a second measurement being above a threshold to determine the presence of ischaemia. For example, in such embodiments a concentration threshold may be in the range 2 µM to 4 µM, and the rate of change threshold may be in the range 1 µM to 8 µM between a first and a second measurement, or a rate of change in the range 1 µM to 8 µM per year.

In some embodiments the concentration is measured by a biosensor responsive to the said one or more purines. The biosensor may be an enzyme sensor, comprising one or more enzymes for which one of the said purines is a substrate. The biosensor may be sensitive to two or more said purines, such that the biosensor provides a signal representative of the total concentration of the two or more purines.

A concentration of a first purine may be measured as the difference between the signal from a biosensor responsive to both a first and a second purine and that from a biosensor responsive to the second purine alone.

A concentration as described herein may be represented by a signal from a biosensor sensitive to one or more purines, and a measurement of a concentration may comprise measuring the said signal and comparing the signal to a calibration value relating the signal to a known concentration of the said one or more purines.

Comparison of a measured concentration of one or more purines with a threshold concentration may be done by comparing a signal from a biosensor sensitive to the said one or more purines with a value of the said signal representative of the threshold concentration.

The concentration may be measured using a biosensor comprising an enzyme electrode comprising one or more immobilised enzymes, as described for example in U.S. Pat. No. 8,417,314 and EP1565565. Examples of suitable enzyme electrodes include:

(1) ATP may be measured with an enzyme electrode biosensor comprising glycerol kinase and glycerol-3-phosphate oxidase, wherein the glycerol kinase and glycerol-1,3-phosphate oxidase catalyse a reaction of ATP in the sample to form glycerine phosphate and hydrogen peroxide ($H_2O_2$) and the electrode detects the $H_2O_2$ produced in the reaction.

(2) The combined concentration of hypoxanthine and xanthine may be measured with an enzyme electrode biosensor comprising xanthine oxidase, wherein the xanthine oxidase catalyses a reaction of the hypoxanthine to form urate and $H_2O_2$ and the electrode detects the $H_2O_2$ produced in the reaction.

(3) The combined concentration of inosine, hypoxanthine and xanthine may be measured with an enzyme electrode biosensor comprising nucleoside phosphorylase and xanthine oxidase, wherein the nucleoside phosphorylase catalyses a reaction of inosine to form hypoxanthine and the xanthine oxidase catalyses a reaction of the hypoxanthine to form urate and $H_2O_2$ and the electrode detects the $H_2O_2$ produced in the reaction.

(4) The combined concentration of adenosine, inosine, hypoxanthine and xanthine may be measured with an enzyme electrode biosensor comprising adenosine deaminase, nucleoside phosphorylase and xanthine oxidase, wherein the adenosine deaminase catalyses a reaction of adenosine to form inosine, the nucleoside phosphorylase catalyses a reaction of inosine to form hypoxanthine and the xanthine oxidase catalyses a reaction of the hypoxanthine to form urate and $H_2O_2$ and the electrode detects the $H_2O_2$ produced in the reaction.

A concentration of a single purine may be derived form the difference between measurements of the combined concentration of more than one purine as measured by such biosensors as (1) to (4). For example a concentration of adenosine may be derived from the difference between a measurement made by the enzyme electrode (4) above sensitive to adenosine, inosine, hypoxanthine and xanthine and a measurement made by the enzyme electrode (3) above sensitive to inosine, hypoxanthine and xanthine.

The signal from the biosensor may be a value of a current flowing through the electrode, and a measurement may be represented by a current. A threshold concentration may be represented by a threshold current and comparison of a measured concentration with a threshold concentration may be achieved by comparison of the respective currents.

The biosensor signals, such as in the form of a current from the biosensor, may be corrected for interferences not related to purine content by subtraction of a control signal such as a current from a 'null' biosensor as described below, without enzymes in the sensing layer, in contact with the same sample, reference or calibration liquid.

Calibration of a sensor may be done by contacting the sensor with a liquid containing a known concentration of a purine. A purine may be added to a sample to 'spike' the sample to allow calibration. In some embodiments a sensor is sensitive to more than one purine and calibration is done by contacting the sensor with one of the said purines, the response of the sensor to the total concentration of the said purines being derived from the response to the single said calibration purine. For example a biosensor comprising an enzyme electrode (4) as described above that is sensitive to adenosine, inosine, hypoxanthine and xanthine may be calibrated by contacting the sensor with a known concentration of adenosine, the response to the adenosine being used to calibrate the response of the sensor to the remaining purines. In enzyme sensors of this type typically the calibration uses the purine which passes through the entire enzymatic reaction cascade. In this way correct functioning of the enzyme cascade and response to purines that enter further down the reaction cascade are ascertained.

The biosensor may be configured to be equally sensitive to each of the purines that it senses. For example, an enzyme sensor (4) as described above may be configured such that substantially all of the inosine produced in the reaction of adenosine catalysed by adenosine deaminase is reacted by the enzyme cascade to form $H_2O_2$. In this way the sensor may have a substantially equal response to inosine as to adenosine. The same may apply to the reactions of inosine, hypoxanthine and xanthine, such that the sensor is substantially equally responsive to each of the purines. In this way the sensor is configured to measure the total concentration of purines substantially equal to the sum of their individual concentrations.

In some embodiments the relationship between the sensitivities of the sensor to different purines may be known, and may for example be a property of the design of the sensor, such that the sensitivity to a second purine will lie within a range of the sensitivity to the first. In this way the response to a second purine may be derived from the response to a first. For example, the response to inosine, hypoxanthine or xanthine may be a known percentage of the response to adenosine, or may lie within a known range of percentages of the response to adenosine. In some embodiments the response to 'total purines' is the response to all the purines present in the sample, calibrated by the response to a single purine, and the response to an individual purine is not derived.

In some embodiments the body fluid is whole blood, for example peripheral whole blood. Biosensors of the kind referred to in U.S. Pat. No. 8,417,314 and EP1565565, comprising a ruthenium purple mediator, and as exemplified below are suited to rapid measurements in whole blood.

Accordingly, the method may comprise measuring a concentration of one or more purines using a biosensor comprising an electrode having immobilised on it an enzyme for which the said purine is a substrate and a ruthenium purple mediator.

In some embodiments the method comprises:
contacting a biosensor adapted to measure the concentration of one or more purines selected from adenosine, hypoxanthine, xanthine, inosine and ATP, with a reference liquid such as a buffer,
measuring a reference signal at a first elapsed time after the biosensor is contacted with the reference liquid,
contacting the biosensor with a body fluid,
measuring a measurement signal at a second elapsed time after the biosensor is contacted with the body fluid, and
deriving a measurement of the concentration of one or more purines from the measurement and reference signals.

An elapsed time may be selected to be within the range 5 seconds (s) to 600 s, in the range 10 s to 300 s, or in the range 30 s to 180 s, such as 90, 120, 150 or 180 s.

Typically the first and the second elapsed times are substantially the same, such as within 10%, 5% or 2% of each other.

In some embodiments the method comprises:
contacting the biosensor with a liquid comprising a known concentration of a purine measuring the calibration signal at a third elapsed time after the biosensor is contacted with said liquid, and
comparing the measurement signal with the calibration signal to derive a measurement of concentration of one or more purines.

Typically the first, second and third elapsed times are substantially the same, such as within 10%, 5% or 2% of each other.

In some embodiments the method comprises:
subtracting the reference signal from the measurement signal to derive a corrected measurement signal,
subtracting the reference signal from the calibration signal to derive a corrected calibration signal, and
deriving the concentration measurement from the ratio of the corrected measurement signal to the corrected calibration signal.

The calibration liquid may be a buffer comprising a known concentration of a purine or may be a sample from a subject comprising a known concentration of a purine added into the sample.

The method may comprise taking a sample of the body fluid and measuring the amount or concentration of one or more purines in the sample. In some embodiments the sample may be taken by means known in the art, for example using a Vacutainer™ and may be tested immediately without prior treatment of the sample.

The method may comprise instructing the subject to undergo a period of rest before a concentration is measured. The method may comprise instructing the subject to perform and action or exercise before a concentration is measured. The method may comprise measuring a baseline concentration of one or more said purines, then instructing the subject to perform an action or exercise and measuring the same purines during or after the action or exercise and comparing these concentration(s) with the baseline concentration(s).

The method may comprise instructing the subject to undergo a period of fasting before a concentration is measured. The method may comprise instructing the subject to eat or drink before a concentration is measured. The method may comprise measuring a baseline concentration of one or more said purines, then instructing the subject to eat or drink and measuring the same purines after the subject has eaten or drunk and comparing these concentration(s) with the baseline concentration(s).

In some embodiments the invention provides a method of monitoring the response of a subject to a clinical procedure such as surgery or drug therapy comprising measuring the concentration of one or more purines as described herein at one or more intervals after the procedure to determine the efficacy of the procedure in changing the measured concentrations. The method may be used to determine the need for further intervention, such as extended follow-up or a further procedure, or to determine a probability that the subject will need such further intervention. For example, a drop in the measured concentration of purines may indicate success in an intervention to relieve ischaemia.

The method may comprise:
measuring a baseline concentration of one or more said purines, carrying out the clinical procedure,
measuring a concentration of the said one or more purines at one or more intervals after the procedure
comparing a concentration with the baseline concentration, wherein a difference between the said concentrations is used to determine the a change in the degree of ischaemia present in the subject.

The method may comprise:
measuring a baseline trend in concentration over time of one or more said purines, carrying out the clinical procedure,
measuring a concentration of the said one or more purines at one or more intervals after the procedure,
comparing a trend in concentration after the procedure with the baseline trend, wherein a difference between the said trends is used to determine the a change in the degree of ischaemia present in the subject.

The measured concentration may be compared with a threshold value to determine the success or otherwise of the procedure.

A change in the degree of ischaemia present in the subject may be used to determine for example one or more of a measure of success of the procedure, a probability that the subject will need further intervention and a risk that the subject may go on to develop an acute ischaemic medical condition.

According to a second aspect the invention provides a device configured to carry out a method as described herein. Typically the device comprises a biosensor adapted to measure the concentration of one or more purines in a body fluid, the purines being selected from adenosine, inosine, hypoxanthine, xanthine and ATP.

The biosensor may comprise an enzyme electrode having immobilised on it an enzyme for which one of the said purines is a substrate and a ruthenium purple mediator, for example an enzyme electrode responsive to all four of adenosine, inosine, hypoxanthine and xanthine, for example as disclosed in U.S. Pat. No. 8,417,314.

In some embodiments the device is configured to carry out a method as described herein to determine the presence of ischaemia in, or to measure a probability that ischaemia is present in, a subject, or the risk of a subject later developing an acute ischaemic disorder.

In some embodiments the device further comprises a controller configured to measure signals from the biosensor and to:
measure a reference signal at a first elapsed time after the biosensor is contacted with a reference liquid,
measure a measurement signal at a second elapsed time after the biosensor is contacted with a body fluid, and
derive the measured concentration of the one or more purines from the said signals.

Typically the first and the second elapsed times are substantially the same.

In some embodiments the controller is configured to:
measure a calibration signal at a third elapsed time after the biosensor is contacted with said liquid, and
compare the measurement signal with the calibration signal to derive the measured concentration of the one or more purines.

Typically the first, second and third elapsed times are substantially the same.

In some embodiments the controller is configured to:
subtract the reference signal from the measurement signal to derive a corrected measurement signal,
subtract the reference signal from the calibration signal to derive a corrected calibration signal, and
derive the measured concentration of the one or more purines from the ratio of the corrected measurement signal and the corrected calibration signal.

In some embodiments the device comprises a liquid receiving element to receive and retain a body fluid from the subject and a biosensor in fluid communication with the liquid receiving element. The liquid receiving element may comprise a portion of a surface of a biosensor on which an enzyme electrode is provided. The liquid receiving element may comprise a test chamber and a biosensor may be provided within the test chamber. The device may comprise an inlet port to allow the reference liquid and the sample to be introduced into the test chamber. The device may be configured to receive a reference liquid and a sample introduced by a user, and to read a signal from the biosensor at a selected elapsed time after the liquid is introduced. The device may be configured to introduce a reference liquid into the test chamber and to introduce the sample into the test chamber under control of the controller. In some embodiments the device is configured to introduce a calibration liquid into the test chamber. The device may comprise one or more fluidic channels opening to the test chamber through which liquids such as the sample, reference and calibration liquids may be introduced. The device may comprise fluid actuation means such as a pump to cause the liquids to flow into the test chamber, and may comprise reservoirs for liquids each connected to the test chamber via a fluidic channel and optionally via a valve.

The device may comprise a controller to control the device and to implement the methods of the invention. The controller may control the flow of liquids and the measurement of purines and may compare measurements with threshold values as described herein. The device may report the purine measurements and may communicate data from the purine measurements, or from the comparison with threshold values to a remote receiving device such as a computer. The controller may be computer-implemented and may comprise a processor and instructions stored in a data store to control operation of the device.

The device may be configured to inter-fit with a sampling device, such as a Vacutainer™, as disclosed for example in pending international patent application WO2014087137. The device may be configured to take a sample from a subject, such as a blood sample, and to contact a biosensor forming part of the device with the sample as described herein.

Preferred features of the second aspect of the invention are as for the first aspect mutatis mutandis

BRIEF DESCRIPTION OF THE FIGURES

FIG. 4 shows the response of sensors as used in the example for inosine (Ino) and hypoxanthine (Hx) relative to the response to adenosine (Ado): (a) mean and SD of the response of 5 sensors normalised to the response of each sensor to adenosine; (b) response against time for one of the sensors in which response to inosine is close to that of adenosine and response to hypoxanthine is greater; (c) examples of combinations of micromolar concentrations of adenosine, inosine and hypoxanthine in a sample and the resulting measured 'total purine' concentration expressed as an equivalent micromolar concentration of adenosine, for sensors having the relative responses shown in (a).

DESCRIPTION OF AN EMBODIMENT OF THE INVENTION

Figure 1:
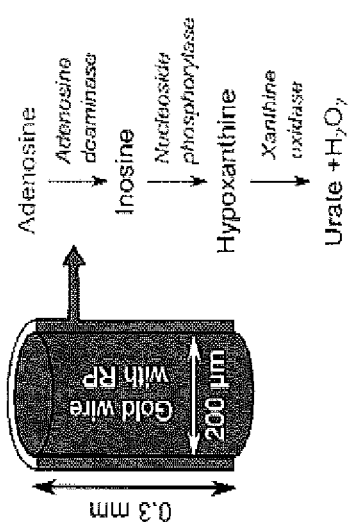
FIG. 1 shows a diagram of a sensing electrode forming part of an enzyme sensor usable to carry out the method, showing an enzymatic cascade used to detect the blood purines. The enzymes are entrapped within a layer on a Ruthenium Purple (RP) coated gold electrode.

In an embodiment the invention provides a method of determining the presence of ischaemia in a subject comprising:
measuring the concentration of a plurality of purines in a body fluid of the subject, the purines being adenosine, hypoxanthine, xanthine, and inosine, and
comparing the measured concentration with a threshold concentration of the one or more purines,
wherein the threshold concentration is in the range 2 µM to 4 µM and a measurement of the total concentration of the purines greater than the threshold concentration indicates the presence of ischaemia.

In this embodiment the method comprises measuring the concentration of adenosine, inosine, hypoxanthine and xanthine using a biosensor responsive to all four said purines. The biosensor comprises (i) an enzyme electrode of type (4) as described previously and in U.S. Pat. No. 8,417,314 and (ii) a null sensor comprising an electrode identical to the enzyme electrode but without enzymes, to correct for background signals from liquid in contact with the biosensor, the signal from the biosensor at any given time being the difference between the enzyme electrode current and the null sensor current at that time. The enzyme electrode is calibrated with a single concentration of adenosine and the ratios of the response to the other three purines to that of adenosine are determined by the characteristics of the electrode, such as dimensions, physical and chemical properties of the enzyme layer and activity of the enzymes provided within them. The measured concentration is expressed as an equivalent concentration of adenosine as described previously, and is referred to below and in the example as a measurement of 'total purines'.

FIG. 4a shows the mean and SD of the response of five sensors of this kind as used in the example to inosine (ino) and hypoxanthine (hx) relative to the response of each sensor to adenosine (ado). From such data the response of the sensor can be related to the total purine content in the sample, allowing the overall response to be calibrated in terms of adenosine. For the example in FIG. 4a, the ratio b as described above for inosine response is around 1.15 and the ratio c for hypoxanthine response is around 1.80. Xanthine oxidase catalyses the reaction of hypoxanthine to form xanthine and $H_2O_2$, and then the reaction of xanthine to form urate and further $H_2O_2$, the electrode detecting the $H_2O_2$ produced in the reaction, so for electrodes of this kind the response to hypoxanthine will be close to twice that to xanthine. Ratio d will therefore be around 0.9.

FIG. 4b shows the response against time for a sensor in which response to inosine is close to that of adenosine and response to hypoxanthine is greater. It can be seen that the time courses of response to each purine overlie each other, allowing the relative responses at any time point to be determined simply as the difference between the trace in the presence of purine and the trace in PBS, and the response to that purine at any time point to be calibrated by the response to adenosine at the same time point.

In this way the 'total purine' response as described herein may be related to either known individual concentrations of the said purines, or a total known concentration of all of the said purines, present in the sample, to provide a measurement of the 'total purine concentration', in terms of an equivalent concentration adenosine, calibrated by a response to single purine such as adenosine.

FIG. 4c gives examples of the combinations of micromolar concentrations of adenosine, inosine and hypoxanthine that may be present within the sample and the resulting measured 'total purine' concentration, expressed as an equivalent micromolar concentration of adenosine, for sensors having the relative responses shown in FIG. 4a. It can be seen that for a range of combination of the concentrations of individual purines, the measured total purine concentration may lie in the range around 2 µM to around 8 µM.

It will be seen in the example below that comparison of the total purine concentration measured and calibrated in this way, with a threshold for the total purine concentration, where the threshold lies in the range 2 µM to 4 µM, is effective to indicate the presence of ischaemia in a subject, and that measurement of individual purine concentrations is not required.

In some embodiments the measured concentration may be used to determine a probability that the subject has a chronic ischaemic medical condition or to determine a degree of risk that the subject may later develop an acute ischaemic medical condition. The probability or risk may be expressed as a higher or lower probability or risk, based on the measured concentration.

The method may comprise using the measured concentration to allocate a subject to a first population having a lower probability of a chronic ischaemic medical condition or a lower degree of risk of developing an acute ischaemic medical condition, or a second population having a higher said probability or risk.

Referring to FIG. 3c (right), it will be seen that subjects of Type 3 have a raised level of total purines (adenosine, hypoxanthine, xanthine, and inosine) pre-operatively, and have an increased risk of cerebral hypoxia during clamping of the carotid artery in a carotid endarterectomy procedure, probably owing to vascular occlusion elsewhere in the cerebral circulatory system, as shown by unconsciousness occurring while the clamp is in place. These patients therefore demonstrate an increased risk of developing an acute cerebral ischaemic condition. The raised level of total purines is such that a threshold concentration selected in the range 2 µM to 4 µM would detect these patients. Referring to FIG. 3b (right) it will be seen that two patients of type 2 would also be selected by such a threshold, and these are likely to have a similar occlusion, except less severe, to those patients in type 3 as indicated by the large increase in purine levels during the procedure. Patients of type 1, who have a small change in total purine level during the procedure, and hence are categorised as having less restricted cerebral vascular flow and hence lower risk of developing an acute cerebral ischaemic condition, have pre-operative purine levels of less than 4 µM. Further, one type 1 patient for whom the pre-operative level is at the top end of the type 1 range at 4 µM experienced a very much larger rise in purine level during the procedure than other type 1 patients and so may be categorised as having a greater restriction of cerebral vascular flow than the others, and therefore may usefully be detected also by a threshold in the range 2 µM to 4 µM.

In this way the embodiment provides a 'wellbeing' test, in which the purine concentration in human subjects may be measured, and the subjects may be allocated to a higher risk population for whom further diagnostic tests or therapy is indicated, or a lower risk population for whom such procedures are not necessary at the time of the test.

The method according to the invention and according to this embodiment will now be illustrated by the following non-limiting example.

EXAMPLE

Microelectrode biosensors were used to measure the purine levels in untreated freshly drawn arterial blood from 18 consented patients undergoing awake carotid endarterectomy (CEA) under local anaesthetic. Samples were measured preoperatively, on exposure of the carotid artery, during the clamp phase, and during the recovery phase following removal of the clamp. The neurological status of each patient was recorded during the procedure.

Surgical Procedures

All CEAs were performed under loco-regional anaesthesia. The procedures were carried out using 3.5 time magnification and a selective shunt and patch policy was used. Before clamping of the carotids intravenous heparin was administered, using a fixed dose of 4000 units. Post operatively the patients were recovered overnight in a PACU (post anaesthetic care unit). Transcranial Doppler was used to assess post-operative cerebral micro-embolisation (Saedon M, et al. Registry report on kinetics of rescue antiplatelet treatment to abolish cerebral microemboli after carotid endarterectomy, Stroke 2013; 44(1): 230-3.14).

Neurological Assessment

Shunting was determined by awake-testing, the indication for shunting being profound neurological obtundation, or significant confusion, restlessness, or inability to respond to commands as determined by continuous clinical assessment by the anaesthetist. Profound deteriorations that occurred within the first 90 s were handled by declamping the artery and allowing the deficit to recover. The operation was then continued under general anaesthesia so that the carotid shunt could be inserted in a controlled fashion. A deficit that occurred more than 90 s after cross-clamp, but before the carotid arteriotomy (trial clamp for 5 minutes), was handled by temporary clamp release. Once normal neurology was restored, clamps were then reapplied allowing a shunt to be inserted before the patient became obtunded a second time (Imray C H et al. Oxygen administration can reverse neurological deficit following carotid cross-clamping. Br J Anaesth 2005; 95(2): 274; author reply 5).

Blood Sampling

An arterial line was inserted under local anaesthetic into the contralateral radial artery as part of the routine intra- and post-operative monitoring. Blood samples were drawn from this line in the anaesthetic room prior to surgery, during the exposure phase, prior to cross clamping, during the cross clamp phase, post clamp release, during closure and in the PACU.

Biosensor Measurements

Microelectrode biosensors as described in Tian F, Llaudet E, Dale N. Ruthenium purple-mediated microelectrode biosensors based on sol-gel film. Anal Chem 2007; 79(17): 6760-6, were used to measure the purines in fresh unprocessed blood. In brief these gold electrodes are coated with a Ruthenium Purple layer, which acts as a mediator to provide the necessary selectivity against interferences such as ascorbate, urate and acetaminophen. This allows the accurate measurement of purines in whole blood.

The purine sensor has an enzymatic layer containing a cascade of three enzymes as shown in FIG. 1 and referred to above as type (4), which allows it to detect all of the substrates for these enzymes: adenosine, inosine, hypoxanthine and xanthine (Tian F. et al. 2007 op. cit.; Llaudet E, Botting N P, Crayston J A, Dale N. A three-enzyme microelectrode sensor for detecting purine release from central nervous system. Biosens Bioelectron 2003; 18(1): 43-52). Amperometric measurements were made to detect the electroreduction of peroxide produced by the final enzyme in the detection cascade, xanthine oxidase. A "null" biosensor recording was used as a control comparison for each experiment. The null biosensors were identical to the purine biosensors in all respects except that they lacked the enzymatic cascade and therefore could not respond to the purines (Frenguelli B G, Llaudet E, Dale N. High-resolution real-time recording with microelectrode biosensors reveals novel aspects of adenosine release during hypoxia in rat hippocampal slices. J Neurochem 2003; 86(6): 1506-15).

Figure 2:
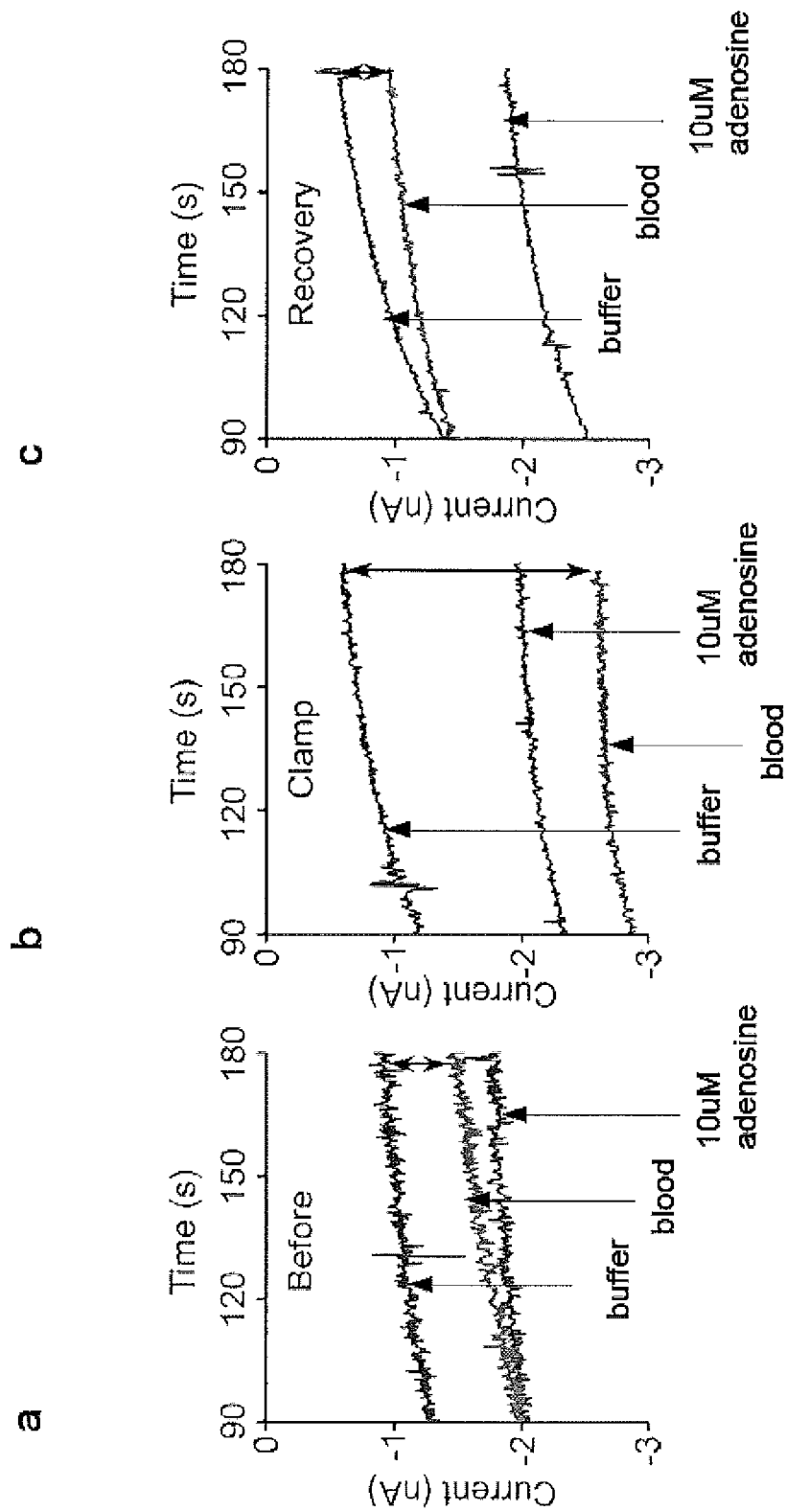
FIG. 2 shows example records of sensor currents during blood measurements from a type 3 patient as discussed in the examples, showing the pre-operative blood purine level, shortly after carotid clamping, and following recovery.

FIG. 2 shows example records of sensor currents during blood measurements from a type 3 patient made (a) pre-operatively, (b) shortly after carotid clamping, and (c) following recovery. The biosensors were polarized to −50 mV with respect to a Ag/AgCl pseudo-reference electrode for 180 s. The current records show the last 90 s of the measurement and are the difference between the purine and null biosensors. The traces show a "zero current" in buffer, calibration with 10 μM adenosine, and measurement in whole blood. The purine concentration in blood is calculated by taking the difference between the blood and buffer traces (black double headed arrows), and expressing this as a proportion of the difference between the calibration and buffer traces.

Both the null and purine biosensors were introduced into the blood sample as soon as possible after sampling. They were simultaneously polarized to the working potential of −50 mV (versus Ag/AgCl), and the amperometric faradaic charging currents recorded as shown in FIG. 2. After 3 minutes the current value of the null sensor was subtracted from the purine biosensor to give the "purine current". This was converted into a purine concentration by comparing it to the current obtained from calibrating the sensors in a known amount of adenosine.

Statistical Presentation and Analysis

All data are presented as medians with 95% confidence limits. In the case of the smaller subgroups of the data (Type 1, 2 and 3 patients) the 95% confidence limits are the same as the range of the data. For the entire group the data was analyzed in a 2 way Friedman ANOVA comparing the pre-clamp, clamp and recovery phase purine levels within each patient, the medians and distributions being compared via the Mann Whitney U test and the Kolmogorov Smirnov tests respectively.

Results

Measurements were collected from 18 patients. First the data obtained from these patients was analysed as a single group. Overall, the median resting purine level in blood, measured pre-operatively, was 2.4 μM (1.3 to 4.0 μM). This value is comparable to others in the literature which suggest that plasma concentrations of hypoxanthine/xanthine (the predominant purines in blood) in humans to be in the range 1-2 μM (Yamamoto T et al. Effect of ethanol and fructose on plasma uridine and purine bases. Metabolism 1997; 46(5): 544-7; Ohno M, et al. Effects of exercise and grape juice ingestion in combination on plasma concentrations of purine bases and uridine. Clin Chim Acta 2008; 388(1-2): 167-72). During the carotid clamping, the blood purine levels rose in every patient relative to the pre-operative baseline. The median purine level in the clamp phase was 6.7 μM (4.7 to 11.5 μM). Following recovery the blood purines fell to the pre-operative baseline (1.9 μM, 1.4 to 2.7 μM). The analysis shows that for the group of patients as a whole within a relatively short period following release of the clamp (less than 2 hours (h)) the blood purine levels are indistinguishable from the pre-operative baseline.

Inspection of the profile of repeated sequential measurements of blood purines made throughout the carotid procedure, combined with the concomitant neurological assessment of the patients, enabled the cohort to be divided into three groups: Type 1, Type 2 and Type 3. Type 1 and 2 patients (7/18 and 8/18 respectively), displayed no major neurological symptoms during carotid clamping. However Type 3 patients (3/18) rapidly became unconscious following the clamping of the carotid artery.

Figure 3:
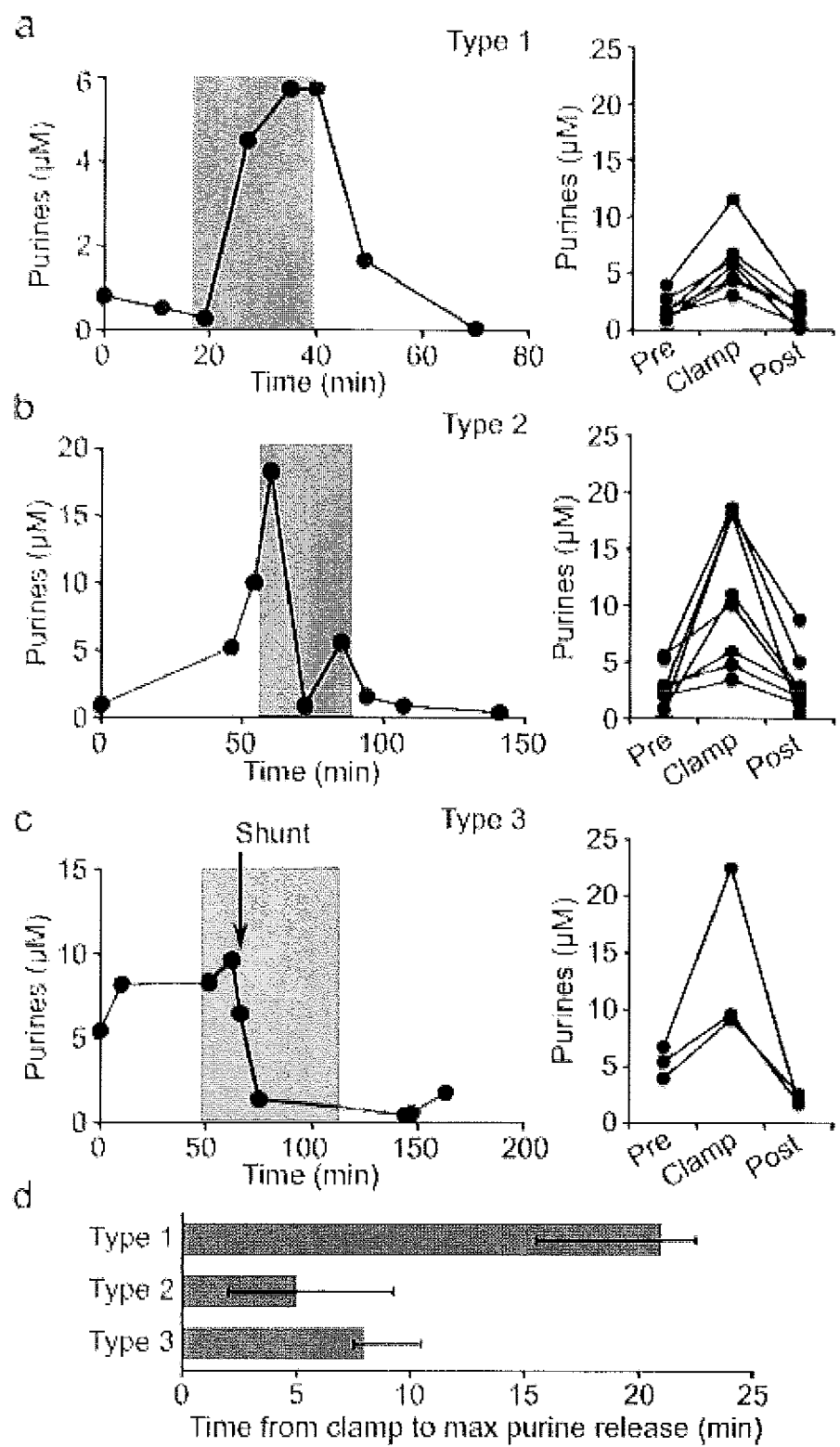
FIG. 3 shows sequential blood purine measurements during carotid endarterectomy for a number of awake patients, revealing different profiles of purine release. a) Left, an example of sequential measurements of blood purine levels in a Type 1 patient. The shaded rectangle indicates the timing and duration of the carotid clamping. Right, plots of the pre-operative, carotid clamp and recovery levels of purines for all Type 1 patients. b) Left, an example of sequential measurements of blood purine levels in a Type 2 patient. Right, plots of the pre-operative, carotid clamp and recovery levels of purines for all Type 2 patients. c) Left, an example of sequential measurements of blood purine levels in a Type 3 patient. Right, plots of the pre-operative, carotid clamp and recovery levels of purines for all Type 3 patients. d) Histograms of the median time from carotid clamp to maximal recorded purine release during the clamp phase for Type 1, 2 and 3 patients.

Results are described with reference to FIG. 3, which shows a) Left, an example of sequential measurements of blood purine levels in a Type 1 patient. The shaded rectangle indicates the timing and duration of the carotid clamping. Right, plots of the pre-operative, carotid clamp and recovery levels of purines for all Type 1 patients. b) Left, an example of sequential measurements of blood purine levels in a Type 2 patient. Right, plots of the pre-operative, carotid clamp and recovery levels of purines for all Type 2 patients. c) Left, an example of sequential measurements of blood purine levels in a Type 3 patient. The patient lost consciousness shortly after application of the carotid clamp, necessitating rapid installation of a carotid shunt (arrow) to restore cerebral blood flow. Note how purine levels rapidly dropped following installation of the shunt. Right, plots of the pre-operative, carotid clamp and recovery levels of purines for all Type 3 patients. d) Histograms of the median time from carotid clamp to maximal recorded purine release during the clamp phase for Type 1, 2 and 3 patients. Error bars are upper and lower quartiles.

In Type 1 patients, the rise in purine levels was sustained throughout the clamp period and reached its maximum towards the end of the clamp period (FIG. 3a). In these patients the median time to maximal purine blood level was 21 minutes (14 to 29 minutes, FIG. 3d). For Type 1 patients the median preoperative purine level was 1.5 μM (0.8 to 4.0 μM). During carotid clamping it rose to 5.7 μM (3 to 11.5 μM) and during the recovery period it fell to 1.8 μM (0.05 to 3.1 μM, FIG. 3a).

Type 2 patients had preoperative baseline purines of 2.4 μM (0.7 to 5.6 μM), and they exhibited a transient pattern of purine release during the carotid clamping. Their blood purines reached a peak (10.0 μM, range 3.4 to 18.6 μM) much quicker than Type 1 patients (3 minutes, 1 to 16 minutes, p=0.001, Mann Whitney U test compared to Type 1 patients, FIGS. 3b, 3d). After reaching this peak, the blood purine levels declined, but in 6/8 cases remained higher than the pre-operative baseline (3.2 μM, 0.9 to 13.6 μM). On recovery the purine levels returned to 2.2 μM (0.4 to 8.7 μM, FIG. 3b)

Type 3 patients (n=3) rapidly became unconscious following carotid clamping. The baseline purine levels were elevated compared to the Type 1 and Type 2 patients (5.4 μM, 3.9 to 6.7 μM, FIGS. 3c, 3d). The purines rose on clamping to 9.6 μM (9.1 to 22.5 μM), before falling to 1.8 μM (1.8 to 2.6 μM) during recovery following the procedure. This recovery value was lower than the preoperative baseline value. Importantly, when the carotid artery was shunted to restore cerebral blood flow, the blood purine levels dropped to below the pre-operative baseline levels (1.4 μM, 0.4 to 2.9 μM). This observation suggests that the brains of these patients are chronically ischaemic owing to impeded carotid blood flow, which was relieved by the shunt (hence the purine levels fell), and also in the longer term by the outcome of the operation.

Discussion

CEA is performed to reduce the risk of a future stroke. As the timing and release of the carotid clamp and hence the ischemic insult is defined, this procedure provides an excellent opportunity to test in human patients whether purine levels in blood are a marker of cerebral ischaemia. In all 18 patients purine levels in arterial blood rose within minutes of applying the carotid clamp. In most patients this occurred in the absence of any major neurological indication. This shows that the purines are a very sensitive measure of cerebral ischaemia. Elevated purine levels were observed throughout the clamp period, demonstrating that the purines are continually produced and released from brain while the ischaemic insult persists. Following release of the clamp, the blood purine levels returned relatively quickly (within 1-2 hours) to the pre-clamp baseline. The purines are thus a relatively short lasting indication of cerebral ischaemia. This implies that the purines could be used firstly, to detect incidence of cerebral ischaemia from its earliest origins and secondly, to monitor the persistence of the ischaemic insult.

The patients in these examples were separated into 3 groups based on their purine release profiles during the procedure, and whether they lost consciousness. Type 1 patients, because they exhibit a rather slower increase in blood purines, may retain a higher ability than either of the other two patient groups to compensate for the loss of blood flow from the ipsilateral carotid artery by enhancing flow from the contralateral side via the Circle of Willis. In type 1 patients, the compensatory flow has a rapid onset coincident with the restriction of blood flow on the ipsilateral side, and this has the effect of slowing and limiting the purine rise during carotid clamping.

The results suggest that type 2 patients may retain some ability for contralateral compensation but that the onset of the compensation is delayed—hence the tendency to higher initial increases in blood purines, and the later fall of purine levels during the clamp phase.

Type 3 patients rapidly lost consciousness during carotid clamping. The results suggest that they have lost the ability to compensate with enhanced blood flow from the contralateral side. Furthermore as their blood purines were high even at the pre-operative stage, their brains may be under chronic ischaemic stress.

The example shows that for type 3 patients, having chronic ischaemic stress, the elevated pre-operative purine levels compared with healthy levels of typically around 1 μM may be used to indicate the presence of chronic cerebral ischaemia. The pre-operative levels in these patients of 5.4 μM (3.9 to 6.7 μM) would be above a threshold concentration in the range 2 μM to 4 μM. Type 2 patients may represent a continuum with the type 3 patients, except that their degree of loss of contralateral compensation is less, and so did not experience unconsciousness. They had pre-operative purine levels in the range 0.7 to 5.6 μM, such that the patients at the high end of this range very likely suffered chronic ischaemia similar to that for patients in type 3, which would be indicated successfully using a threshold in the range 2 μM to 4 μM. A threshold in the range 2 μM to 4 μM is therefore usable to indicate a patient having a chronic degree of ischaemia, and as shown by this example to be usable to indicate a patient at higher risk of developing an acute ischaemic condition, and to prioritise the patient for further diagnostics.

As shown by the results for the type 3 patients, a higher threshold concentration, such as in the range 4 μM to 8 μM, might be used to indicate a more serious degree of ischaemia, and may be used in a method to prioritise such patients for immediate further diagnostic or therapeutic procedures.

The example shows that a change in a measured concentration over time may show a change in the degree of ischaemia in a patient, such as an increase in the severity of ischaemia as in the case of carotid arterial clamping, a reduction in the degree of ischaemia following restoration of cerebral blood flow following CEA. In this way measurement of purines according to the invention may indicate a change, either an increase or decrease in the degree of ischaemia and therefore a change in a degree of risk of developing a subsequent acute ischaemic condition.

The invention has been described by way of examples only and it will be appreciated that variation may be made to the above-mentioned embodiments without departing from the scope of invention.

With respect to the above description then, it is to be realised that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

The invention claimed is:

1. A method of determining a predisposition to a chronic ischaemic condition or an acute ischaemic condition associated with ATP depletion in a subject, the method comprising:
   a. measuring the concentration of one or more purines in a body fluid of the subject using a biosensor comprising an electrochemical cell, where the purines are selected from the group consisting of adenosine, inosine, hypoxanthine, xanthine, and ATP, and
   b. comparing the measured concentration with a threshold concentration of the one or more purines, wherein the threshold concentration is in the range from about 2 μM to about 8 μM, and wherein a measured concentration higher than the threshold concentration indicates the presence of the condition.

2. The method of claim 1 wherein the condition associated with ATP depletion is a chronic ischaemic condition selected from the group consisting of cerebral ischaemia resulting from vascular disease, cardiovascular disease, chronic ischaemic heart disease (IHD) characterized at least by angina and ischaemic cardiomyopathy, critical limb ischaemia (CLI), hypoxic tumours in cancer, and bedsores in immobile patients, or an acute ischaemic condition selected from the group consisting of ischaemic stroke, transient ischaemic attack (TIA), myocardial infarction (MI), and deep-vein thrombosis.

3. The method of claim 1 wherein the threshold concentration is in the range from about 2 μM to about 4 μM.

4. The method of claim 1 wherein the threshold concentration is in the range from about 4 μM to about 8 μM.

5. The method of claim 1 wherein the measured concentration is the total of the concentrations of two or more single purines each measured individually.

6. The method of claim 5 wherein the one of the purines is adenosine, inosine, xanthine, or ATP, and the threshold concentration is in the range from about 2 µM to about 4 µM; or one of the purines is hypoxanthine, and the threshold concentration is in the range from about 2 µM to about 8 µM.

7. The method of claim 1 wherein the threshold concentration is 2.0, 2.2, 2.4, 2.5, 2.6, 2.8, 3.0, 3.2, 3.4, 3.5, 3.6, 3.8, 4.0, 4.5, 5.0, 5.5, 6.0, 6.5, 7.0, 7.5, or 8.0 µM.

8. The method of claim 1 wherein the body fluid is whole blood.

9. The method of claim 1 wherein the purine concentration is measured using a biosensor comprising an electrode having immobilized on the electrode one or more enzymes for which at least one of the said purines is a substrate, and a ruthenium purple mediator.

10. A device configured to carry out the method of claim 1.

11. The device of claim 10 comprising a biosensor adapted to measure the concentration of one or more purines in a body fluid, where the purines are selected from the group consisting of adenosine, inosine, hypoxanthine, xanthine, and ATP.

12. The device of claim 11 wherein the biosensor comprises an enzyme electrode having immobilized on it an enzyme for which at least one of the said purines is a substrate, and a ruthenium purple mediator.

13. The device of claim 11 wherein the biosensor comprises an enzyme sensor responsive to all four of adenosine, inosine, hypoxanthine, and xanthine.

14. The device of claim 11 further comprising a controller configured to measure signals from the biosensor and configured to:
measure a reference signal at a first elapsed time after the biosensor is contacted with a reference liquid,
measure a measurement signal at a second elapsed time, optionally substantially the same as the first time, after the biosensor is contacted with a body fluid, and
derive the measured concentration of the one or more purines from the said signals.

15. The device of claim 14 wherein the controller is configured to:
measure a calibration signal at a third elapsed time, optionally substantially the same as the first or the second time, after the biosensor is contacted with a calibration liquid, and
compare the measurement signal with the calibration signal to derive the measured concentration of the one or more purines.

16. The device of claim 14 wherein the said first elapsed time is within the range of 5 seconds to 600 seconds.

17. The device of claim 11 further comprising a test chamber, where the biosensor is within the test chamber, and wherein the device is configured to introduce a reference liquid or a calibration liquid into the test chamber and to introduce the sample into the test chamber under control of the controller.

18. The method of claim 1 further comprising:
measuring the rate of change of the concentration of one or more of said purines, and
using the measured concentration and the measured rate of change to determine the presence of the condition in the subject.

19. A method of determining a predisposition to a condition associated with ATP depletion in a subject, the method comprising:
a. measuring an equivalent total purine concentration measured by a measurement device responsive to two or more of said purines, where the purines are selected from the group consisting of adenosine, inosine, hypoxanthine, xanthine, and ATP; and where the total purine measurement is calibrated relative to the response of the measurement to a single calibration purine; and
b. comparing the measured concentration with a threshold concentration, wherein the threshold concentration is in the range from about 2 µM to about 8 µM, and wherein a measured concentration higher than the threshold concentration indicates the presence of the condition.

20. The method of claim 19 wherein the measurement device is responsive to adenosine, inosine, hypoxanthine, and xanthine, and the calibration purine is adenosine.

21. A method of determining a predisposition to a chronic ischaemic condition or an acute ischaemic condition associated with ATP depletion in a subject, the method comprising:
measuring the concentration of one or more purines in a body fluid of a subject at two or more time points using a biosensor comprising an electrochemical cell, where the purines are selected from the group consisting of adenosine, inosine, hypoxanthine, xanthine, and ATP, and deriving the rate of change of the measured concentration, and
comparing the rate of change with a threshold value for the rate of change, where a rate of change above the threshold rate of change indicates that the condition is present.

22. The method of claim 21 wherein the rate of change threshold is in the range from about 1 µM to about 8 µM per year.

* * * * *